United States Patent
Woodbine et al.

(10) Patent No.: US 11,484,898 B2
(45) Date of Patent: Nov. 1, 2022

(54) SYSTEM AND METHOD FOR VAPORIZING CARTRIDGE SYSTEM WITH DIFFUSER

(71) Applicant: GOFIRE, INC., Denver, CO (US)

(72) Inventors: John Jesse Woodbine, Lafayette, CO (US); Joseph Francis Keenan, Superior, CO (US)

(73) Assignee: GOFIRE, INC., Denver, CO (US)

( * ) Notice: Subject to any disclaimer, the term of this patent is extended or adjusted under 35 U.S.C. 154(b) by 500 days.

(21) Appl. No.: 16/541,062

(22) Filed: Aug. 14, 2019

(65) Prior Publication Data
US 2020/0060342 A1 Feb. 27, 2020

Related U.S. Application Data

(60) Provisional application No. 62/721,699, filed on Aug. 23, 2018.

(51) Int. Cl.
*A24F 40/48* (2020.01)
*B05B 11/00* (2006.01)
(Continued)

(52) U.S. Cl.
CPC ......... *B05B 11/0002* (2013.01); *A24F 40/10* (2020.01); *A24F 40/30* (2020.01); *A24F 40/42* (2020.01); *A24F 40/48* (2020.01); *A24F 40/485* (2020.01); *A24F 40/50* (2020.01); *B05B 11/0054* (2013.01); *B05B 11/025* (2013.01); *B05B 11/3015* (2013.01); *B05B 11/3074* (2013.01)

(58) Field of Classification Search
CPC .......... A24F 40/48; A24F 40/10; A24F 40/42; A24F 40/485; B05B 11/0002
See application file for complete search history.

(56) References Cited

U.S. PATENT DOCUMENTS 9,320,301 B2 * 4/2016 Memari ................ H02J 50/10
9,877,509 B2 1/2018 Dai et al.
(Continued)

FOREIGN PATENT DOCUMENTS

WO PCT/US19/28541 10/2019

OTHER PUBLICATIONS

PCT International Search Report for International Application PCT/US2019/046951, search report dated Dec. 16, 2019 (dated Dec. 16, 2019).

*Primary Examiner* — Hae Moon Hyeon
(74) *Attorney, Agent, or Firm* — Law Offices Of Daniel W. Roberts; Daniel W. Roberts

(57) ABSTRACT

Provided is a system and method for a vaporizer cartridge system wherein the cartridge provides the diffuser. More specifically, an embodiment of the system includes a vaporizing device providing a heating element proximate to a removable cartridge system receiving port, and a dispenser trigger structured and arranged to engage the removable cartridge to dispense a predetermined amount of a liquid concentrate from within the removable cartridge. The system further includes a cartridge with diffuser including: a housing; a reservoir of liquid concentrate; a diffuser element; a metered dispenser structured and arranged to dispense from the reservoir into the diffuser element a predetermined amount of liquid concentrate. An associated method of use is also provided.

25 Claims, 8 Drawing Sheets

(51) Int. Cl.
    *A24F 40/50*      (2020.01)
    *A24F 40/42*      (2020.01)
    *A24F 40/30*      (2020.01)
    *A24F 40/10*      (2020.01)
    *A24F 40/485*    (2020.01)
    *B05B 11/02*      (2006.01)

(56) References Cited

U.S. PATENT DOCUMENTS

| | | |
|---|---|---|
| 10,092,038 B2 | 10/2018 | Xu |
| 10,279,934 B2 | 5/2019 | Christensen et al. |
| 11,109,622 B1 * | 9/2021 | Woodbine ............... A24F 40/65 |
| 2011/0277757 A1 | 11/2011 | Terry et al. |
| 2016/0106936 A1 | 4/2016 | Kimmel |
| 2016/0309789 A1 * | 10/2016 | Thomas, Jr. ......... A61M 11/042 |
| 2016/0310624 A1 | 10/2016 | Wynalda, Jr. |
| 2016/0360790 A1 * | 12/2016 | Calfee .................... A24F 40/46 |
| 2017/0013884 A1 | 1/2017 | Dai et al. |
| 2018/0140021 A1 * | 5/2018 | Alarcon ................... B05B 1/30 |
| 2019/0037923 A1 | 2/2019 | Shenkal et al. |
| 2019/0091423 A1 | 3/2019 | Tygett |
| 2021/0161213 A1 | 6/2021 | Woodbine |

\* cited by examiner

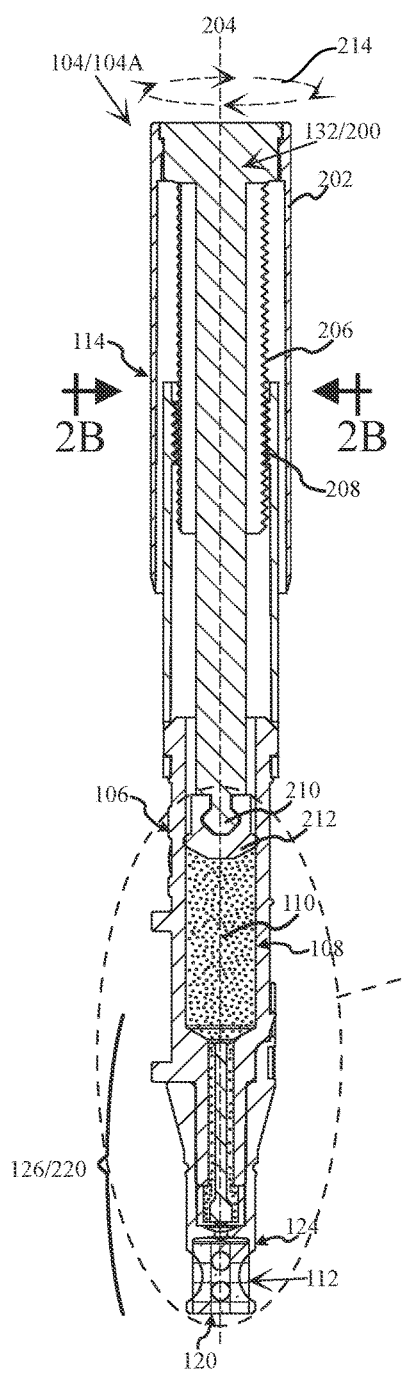
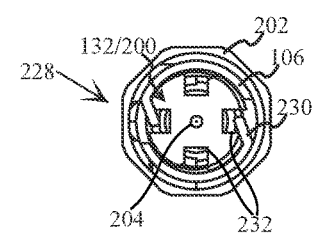
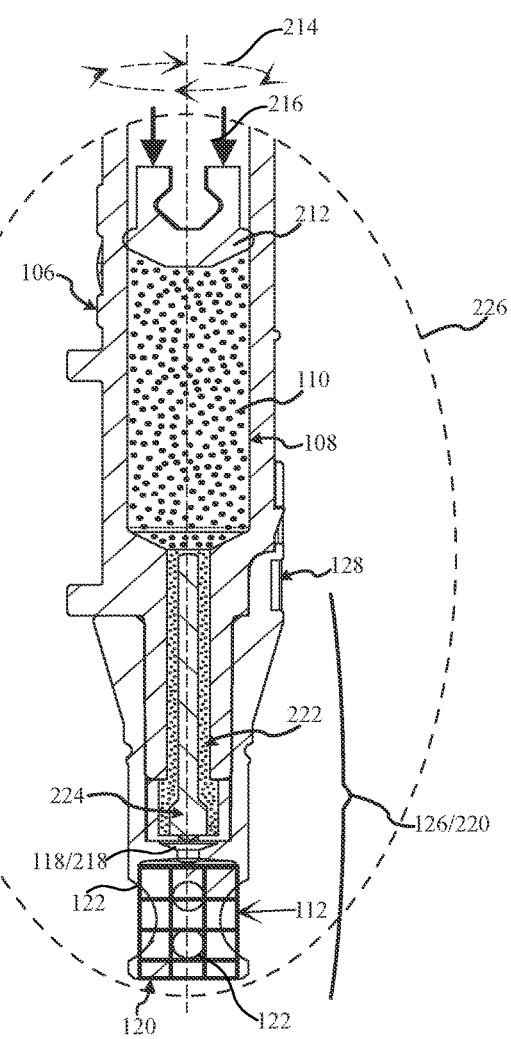
FIG. 2A
FIG. 2B

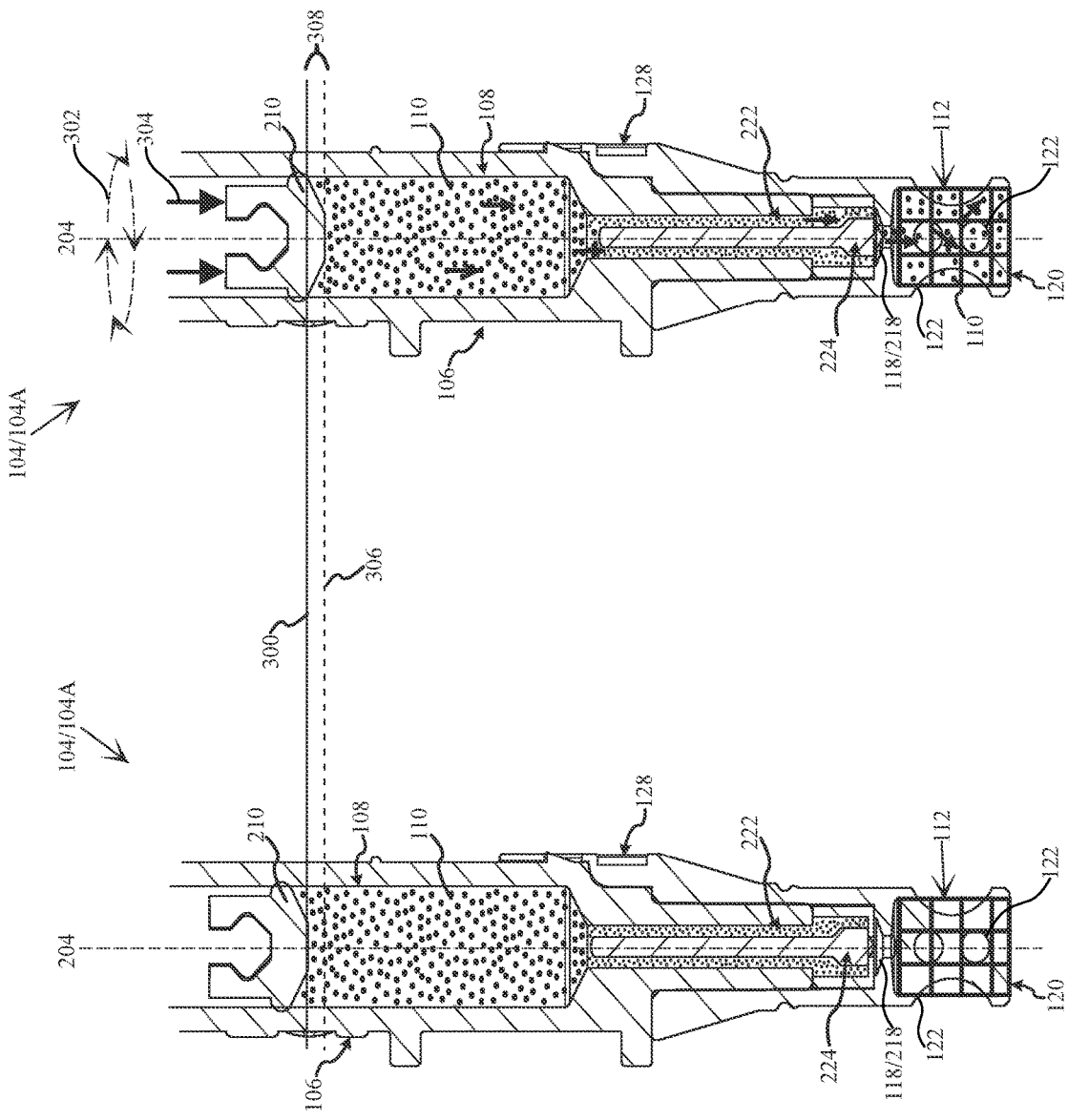

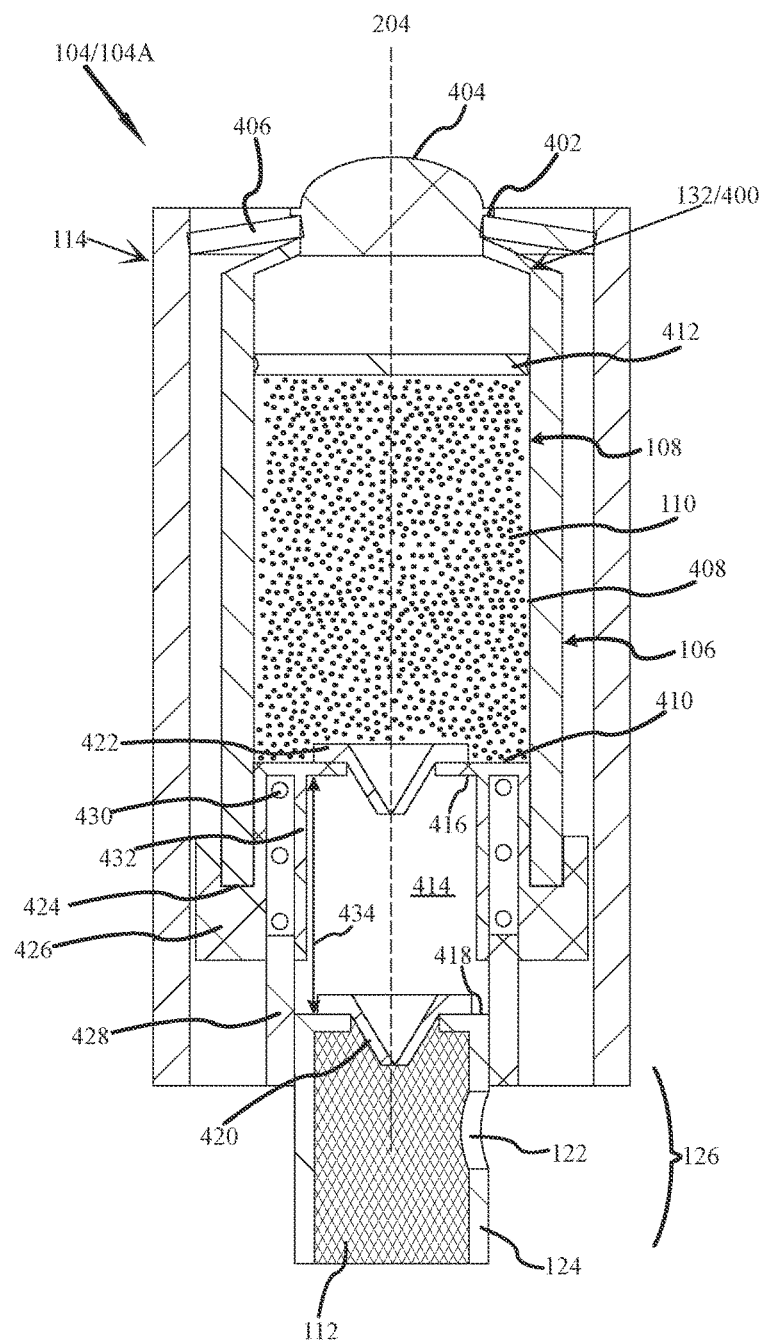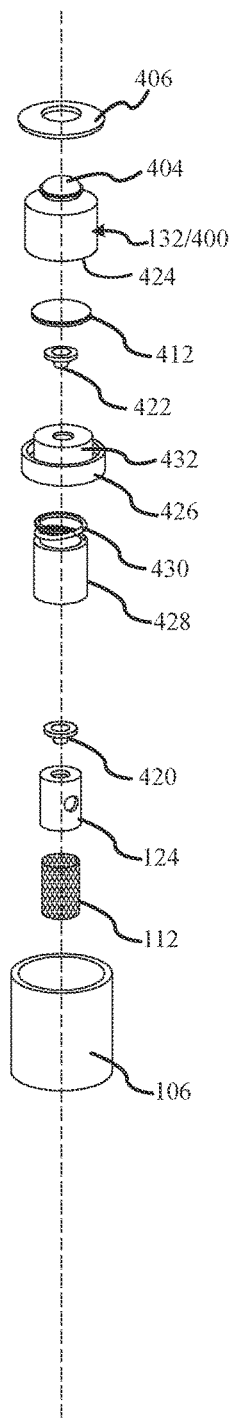

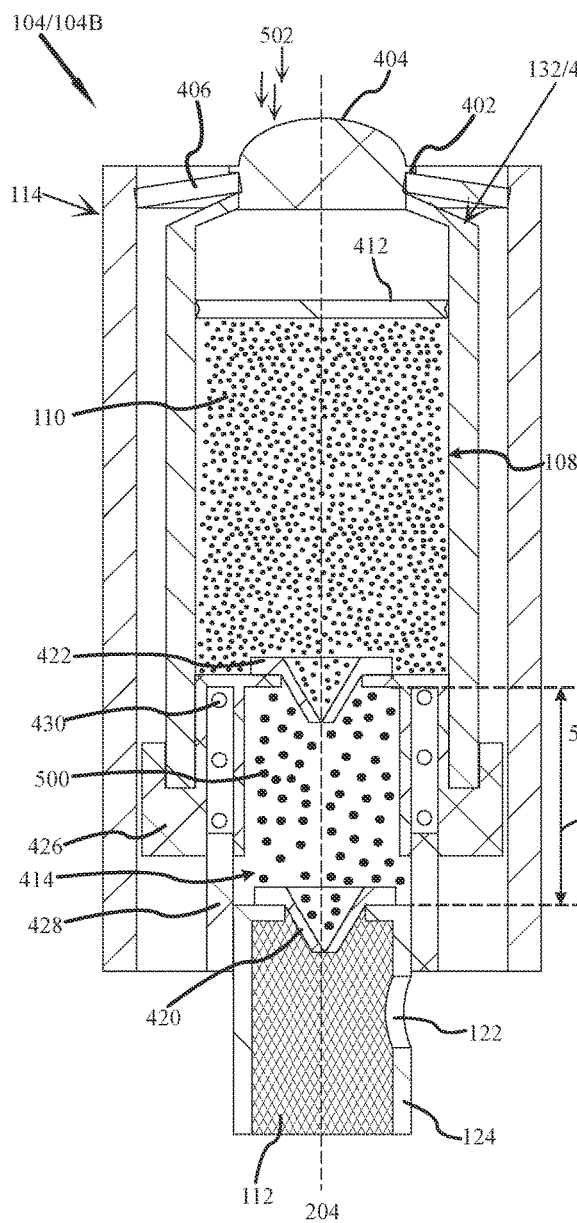
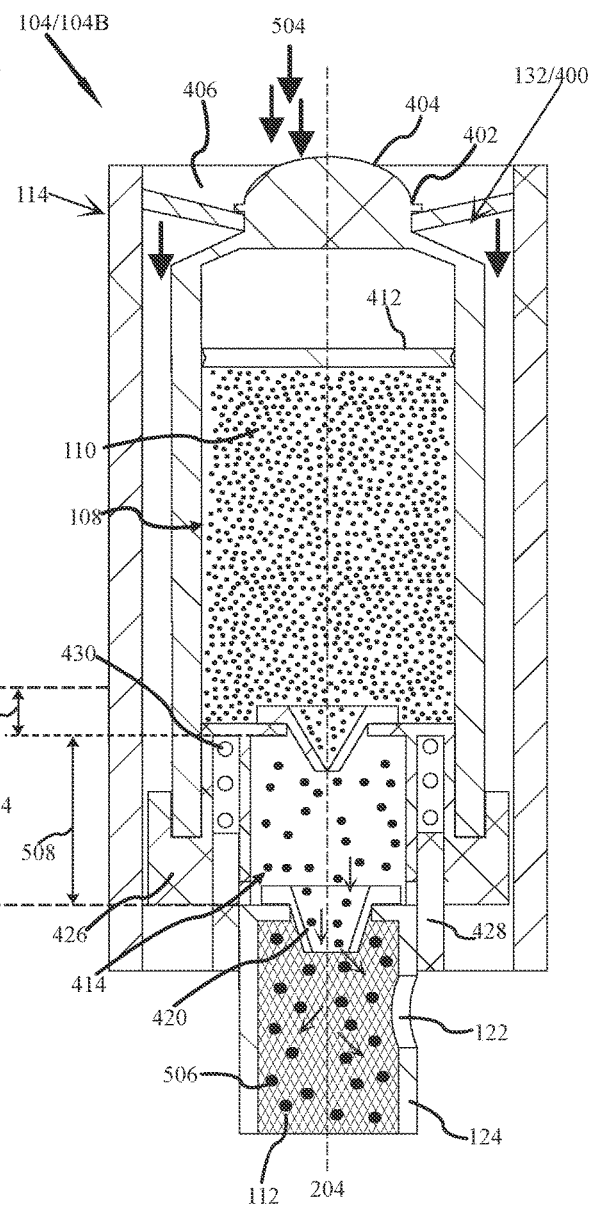
FIG. 5A
FIG. 5B

FIG. 6A
FIG. 6B
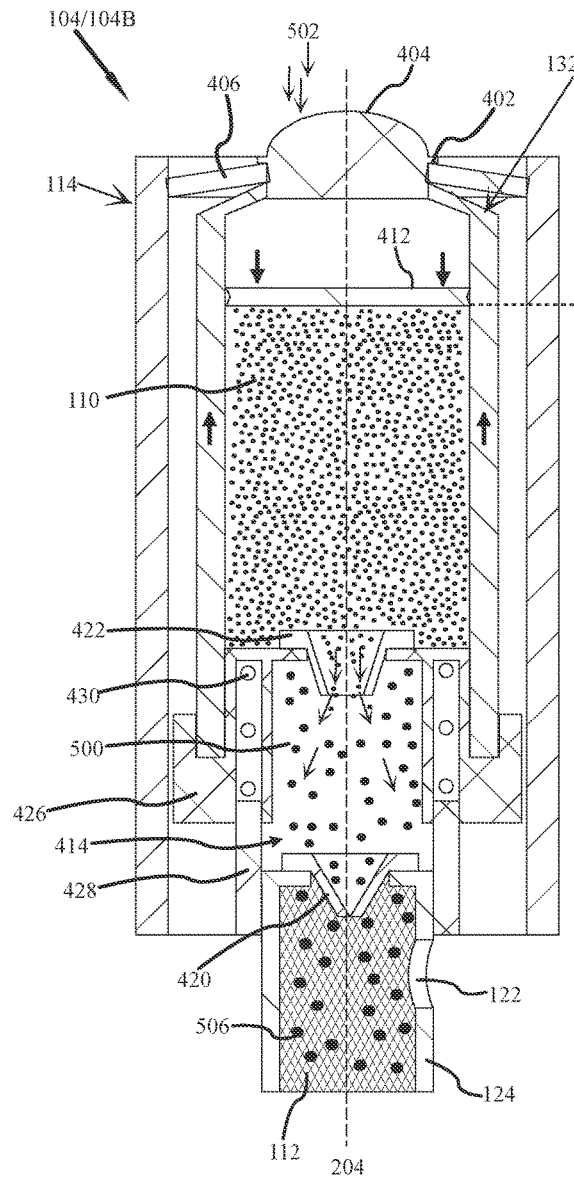
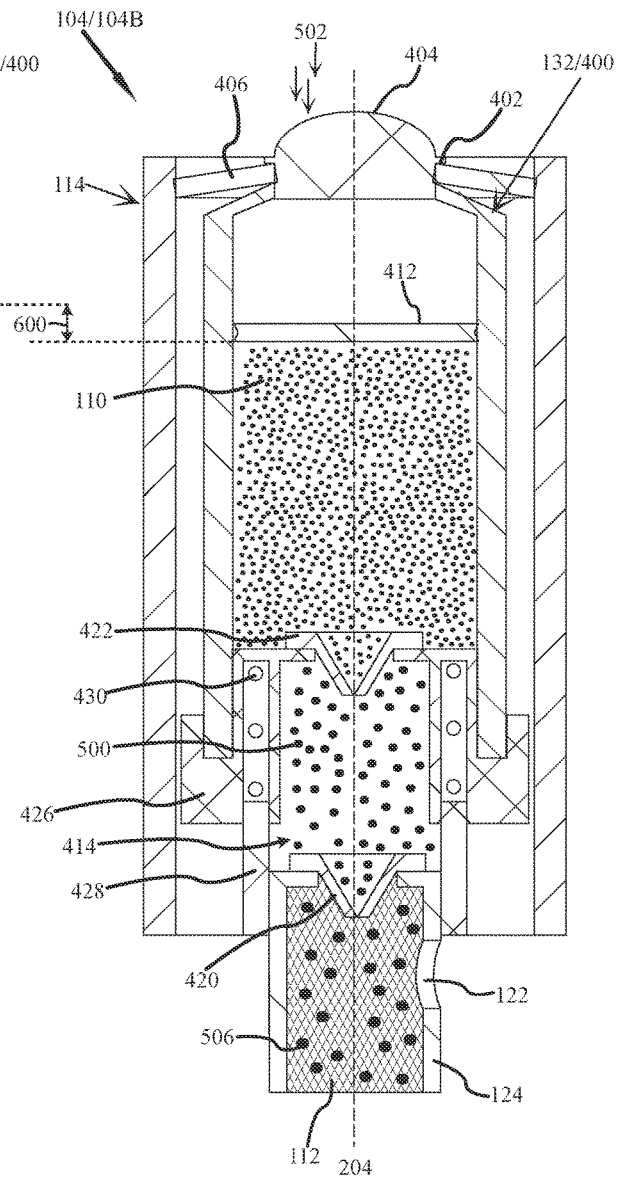

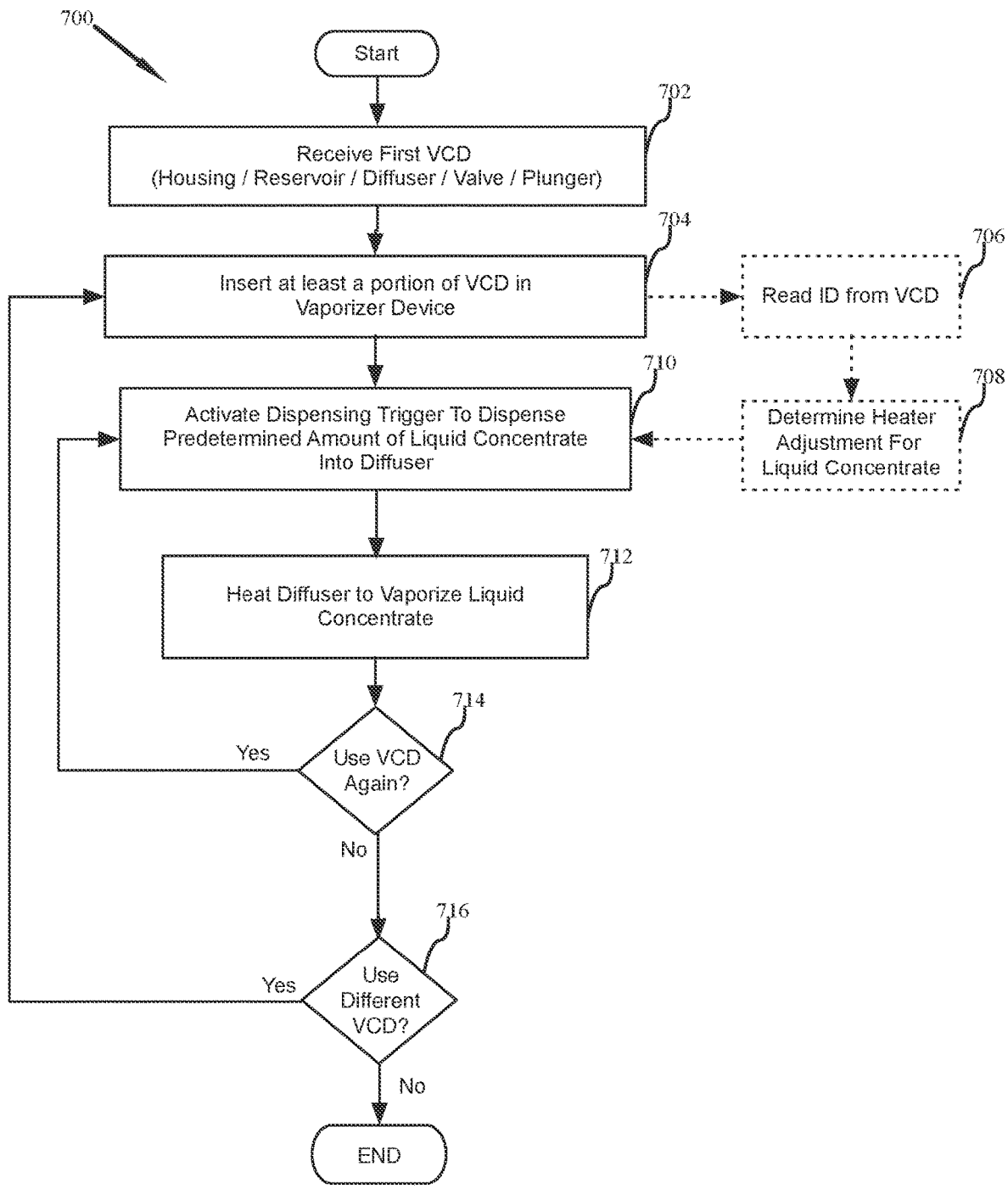

SYSTEM AND METHOD FOR VAPORIZING CARTRIDGE SYSTEM WITH DIFFUSER

CROSS REFERENCE TO RELATED APPLICATIONS

This application claims the benefit under 35 U.S.C. § 119(e) of U.S. Provisional Application No. 62/721,699 filed Aug. 23, 2018 and entitled VAPORIZER CARTRIDGE SYSTEM AND METHOD OF USE, the disclosure of which is incorporated herein by reference.

FIELD OF THE INVENTION

The present invention relates generally to portable hand held vaporizer systems and more specifically to the cartridge devices used therewith for managing and optimizing concentrate materials' vapor quality, device vaporizing efficiency, device quality and manufacturability, vaporizer dosing control and management, and vaporization user experience.

BACKGROUND

Vaporizing devices are readily known and used in medical and recreational settings for dispensing concentrate products (i.e., liquid or semisolid products, such as oils, oil concentrates, and distillates). Current devices allow users to operate a vaporizing device by loading a desired quantity of a concentrate product (optionally pre-packaged in a cartridge unit) into the vaporization chamber/cartridge of the vaporizing device.

Generally, the mechanisms for loading the concentrate are complex to operate, and as a result, the user may end up consuming erratic/inconsistent quantities of the concentrate in vaping sessions and/or damage the cartridge sealing capability causing, for example, improper heating of concentrate material. Furthermore, the user is typically unaware of the concentrate being used owing to lack of availability of information related to the concentrate.

Without limitation to the function of other components of a vaporizer, cartridges are an integral part of the overall operation of many vaporizer devices. The current landscape of vaporizer devices include cartridges that are plagued by the following shortcomings: 1) inability to consistently meter dose, 2) the need to dilute concentrate oils with excipients such as polyethylene glycol in order to facilitate the wicking process, 3) the incorporation of a heater coil that combusts the oil, creating tar elements such as, but not limited to Polycyclic aromatic hydrocarbons (PAH), carbon monoxide and other unhealthy byproducts, 4) the inability to store pertinent information on the cartridge to facilitate appropriate and safe use of the product, 5) in some designs, the lack of a dedicated diffuser to eliminate cross-contamination, 6) the inability to protect the product stored in the cartridge from heat degradation or from excessive wicking during vaporization 7) lack of a means to protect the product within the cartridge from ultra-violet (UV) degradation, 8) too large and space-consuming form factor, making them consumer unfriendly, 9) high manufacturing costs, and 10) the inability to provide capacity for multiple doses.

Currently available vaporizing devices such as Pax 3™ and Firefly 2™ do not have a cartridge-based system, and therefore, rely on the product's package labeling for concentrate information and on the user to meter dose of the product into the device. PotBotic's RYAH™ does provide a cartridge, but RYAH's methodology of metered dose delivery relies on heating the full multi-dose reservoir and monitoring the inhalation of vapor exuded from the cartridge. Unfavorably, this heating methodology cycles the concentrate product within the cartridge which accelerates its degradation.

Also, this dose measuring and delivery methodology does not allow the device to record desirable information back onto the cartridge such as the number of doses remaining. The RYAH also does not allow the vaporizer device to disable the cartridge after full use to eliminate misuse. It is useful to have a vaporizer device, including a cartridge system, with the capability to protect the product contained and to record and distribute information to a user regarding product information like name, distillate fill batch information, laboratory results, product temperature limits, etc. . . .

In light of the aforementioned issues, many vaporizers are not capable of cleanly and accurately dosing concentrate products, and in connection with particular oils, for user inhalation. Vaporizers, such as the Pax 3™, require manual fill, whereby a user must use precision tools, such as metered syringes, to achieve accurately controlled dosing. These tools are difficult to source and contribute additional cost to the vaporizer system.

In the case of vaporizers for medical use, such limitations do not allow users and/or physicians to confidently and consistently administer and/or prescribe concentrate product dose regimens best suited for the user's needs. Some concentrate vaporization devices have addressed dosing issues by utilizing inhaled flow rate as a means to control dosing; however, these products fail to adequately provide uniform vaporization of the concentrates, resulting in a mismatch between prescribed/desired dosage and actual amounts received by the user. Furthermore, vaporizers that utilize cartridges pre-filled with concentrate product—e.g., dose "pod"—are, likewise, limited as the minimum dose is predicated on the volume of the concentrate product in the pod. In view of current vaporizers, there is a need to maintain the operational certainty of vaporizers as it relates to vapor sealing, dose integrity, and corresponding direct user and system feedback at a minimum.

Furthermore, there is a current lack of technology that allows for dosing of different types of concentrate products intended for use in vaporization devices. These materials can be, for instance, paste, thick oil, or other physical materials capable of being portioned and delivered through a vaporizer device. Likewise, most raw materials intended for vaporization vary in consistency, such as in their viscosities, and have not been standardized in a way that can be portioned into uniform doses. Correct dosing of such products is further compromised if loaded by hand or other ill-controlled filling processes. What is needed is an "all-in-one" vaporizer, including a cartridge system that allows controlled uniform dosing and tracking of the chemical compounds of the products contained inside the cartridge regardless of the product's physical form and/or constituents.

Prior art vaporizers use either combustion or convection techniques to vaporize concentrate oils. The concentrate oils' active compounds are delivered more efficiently and without unhealthy levels of byproducts, such as tar (PAH) and carbon monoxide, via convection, and as such, it is the vaporization method of choice. However, convection also presents hurdles as it is more difficult to achieve and maintain a consistent temperature at/of the oil for efficient vaporization using conventional convection techniques.

In one aspect, oil tends to flash and/or wick away to nearby non-functional surfaces when exposed to heat thereby creating a loss of efficiency in current vaporizers. These prior art systems also exhibit overheating after a few uses owing to, among other design set-backs, the tendency to flash and wick away. As such, they require safety circuitry to protect the user from being burned. These currently available vaporizers use various methods in an attempt to provide controlled convection heating to the concentrate oils, including flowing hot air directly to oils contained in heating chambers utilizing limited surface area for flashing. In an attempt to circumvent, the prior art vaporizers dispense oils onto large dosing pads that require excessive heat to vaporize. Batch heating in this manner leads to heating more oil than is required for a desired dose. Such methods contribute to inefficient delivery of the concentrate vapor and degradation of the remaining oil exposed to this heating process.

Prior art vaporizer systems, such as the Pax 3™ and Firefly 2™, also do not provide a feedback system to alert a user that concentrate product has been completely vaporized. Other systems such as PotBotic's RYAH™ provides a dose-measuring methodology; however, the device to record does not capture or record desirable information, such as the number of doses remaining, back onto the cartridge.

Additionally, the RYAH does not provide communication between the vaporizer and its cartridge allowing the vaporizer device to disable the cartridge after full use to, for example, eliminate subsequent misuse of the device. As such it is desirable to allow a user the ability to deliberately select their dose (e.g., micro-dosing) and provide the user notification when they have completed the inhalation of the administered dose or desired amount of concentrate product.

Further still, it is not uncommon for a user to desire different types of concentrated products at different times, especially when such use is for a variety of medical conditions. However, as the vaporizing chamber is traditionally a component of the vaporizing device, when one cartridge is removed and another replaced—the same vaporizing surface or area within the vaporizing chamber is used.

Often the vaporizing area is hard to clean, or may require care and attention that is not always available. As such, build up from prior vaporizations may remain and retard/degrade the quality of the new vaporization effort. More simply, even if the proper volume of concentrated product is provided in the vaporizing chamber, prior remains may prevent full vaporization of the newly deposited concentrate as intended. When such vaporization is not complete, the remaining concentrate only adds to the problematic issue as it too may frustrate the next effort for vaporization of the same or a different product.

Therefore, there is the additional need for a vaporizer device cartridge system, which provides an airtight seal upon loading of the cartridge into the vaporizer device, while also facilitating easier access by users to facilitate cleaning of the device before/after use. It is also desirable that a vaporizer device's cartridge system removes the potential of contamination and cross-contamination of concentrate products, eliminates excessive wicking of concentrate product, provides integrated components to effectively manage dosing of concentrate product while increasing vaporization efficiency, reduce manufacturing and assembly costs of vaporizer devices, control cartridge loading and refill of concentrate product, and minimize volume, weight, and footprint (i.e., overall size) of vaporizing devices.

Hence there is a need for a method and system that is capable of overcoming one or more of the above identified challenges.

SUMMARY OF THE INVENTION

Our invention solves the problems of the prior art by providing novel systems and methods to substantially reduce cross contamination and residue build up between cartridges, while at the same time advantageously ensuring consistent metering of dosage of the concentrate product from the removable reservoir cartridge.

In particular, and by way of example only, according to at least one embodiment, provided is a vaporizer cartridge system including: a vaporizing device providing a heating element proximate to a removable cartridge system receiving port, and a dispenser dispensing trigger structured and arranged to engage the removable cartridge to dispense a predetermined amount of a liquid concentrate from within the removable cartridge; at least one removable cartridge system including: a housing; a reservoir of liquid concentrate; a diffuser element; a metered dispenser structured and arranged to dispense from the reservoir into the diffuser element a predetermined amount of liquid concentrate.

In yet another embodiment, provided is a removable vaporizer cartridge system including: a housing; a reservoir of liquid concentrate within the housing; a diffuser element; a first one-way valve disposed between the reservoir and the diffuser element; a dispensing plunger structured and arranged to apply a pre-determined force upon the reservoir to dispense from the first one-way valve a predetermined amount of liquid concentrate into the diffuser element; wherein the removable cartridge is structured and arranged to be removably disposed within a vaporizing device providing a heating element proximate to the diffuser element, the vaporizing device further providing a dispensing trigger structured and arranged to engage the dispensing plunger of the removable cartridge.

For yet still another embodiment, provided is a removable vaporizer cartridge system including: a housing; an airless pump with a reservoir of liquid concentrate at least partially disposed within the housing; a diffuser element; a mechanical threshold dispensing trigger structured and arranged to require a predetermined threshold force to be applied before the trigger transfers directs force upon the airless pump to dispense a predetermined amount of liquid concentrate into the diffuser element; wherein the removable cartridge is structured and arranged to be removably disposed within a vaporizing device providing a heating element proximate to the diffuser element, the vaporizing device further providing a dispensing trigger structured and arranged to engage the dispensing plunger of the removable cartridge.

And for yet another embodiment, provided is a method of vaporizing liquid concentrate with a portable vaporizing device, including: receiving a first vaporizing cartridge system having; a housing: a reservoir of liquid concentrate within the housing; a diffuser element; a first one-way valve disposed between the reservoir and the diffuser element; a dispensing plunger structured and arranged to apply a pre-determined force upon the reservoir to dispense from the first one-way valve a predetermined amount of liquid concentrate into the diffuser element; inserting at least a portion of the first vaporizing cartridge system into a vaporizing device providing a heating element proximate to a receiving port structured and arranged to receive the at least one vaporizing cartridge system, and a dispenser trigger structured and arranged to engage the dispensing plunger to dispense a predetermined amount of a liquid concentrate from within the removable cartridge into the diffuser element; activating the dispensing trigger to dispense the predetermined amount of liquid concentrate into the diffuser element; and heating the diffuser element to vaporize the liquid concentrate into an air passage conduit from at least the diffuser element to a vapor dispensing port.

BRIEF DESCRIPTION OF THE DRAWINGS AND SUPPORTING MATERIALS

FIG. 2A illustrates a side cut through view of a vaporizing cartridge with diffuser having a screw plunger in accordance with at least one embodiment of the present invention;

FIG. 2B is a top cut through view of a vaporizing cartridge with diffuser having a screw plunger in accordance with at least one embodiment of the present invention;

FIG. 3A is an enlarged partial side cut through of the nozzle area of the vaporizing cartridge with diffuser shown in FIG. 2A at rest in accordance with at least one embodiment;

FIG. 3B is an enlarged partial side cut through of the nozzle area of the vaporizing cartridge with diffuser shown in FIG. 2A providing a metered delivery of liquid concentrate into the diffuser element in accordance with at least one embodiment;

Figure 1:
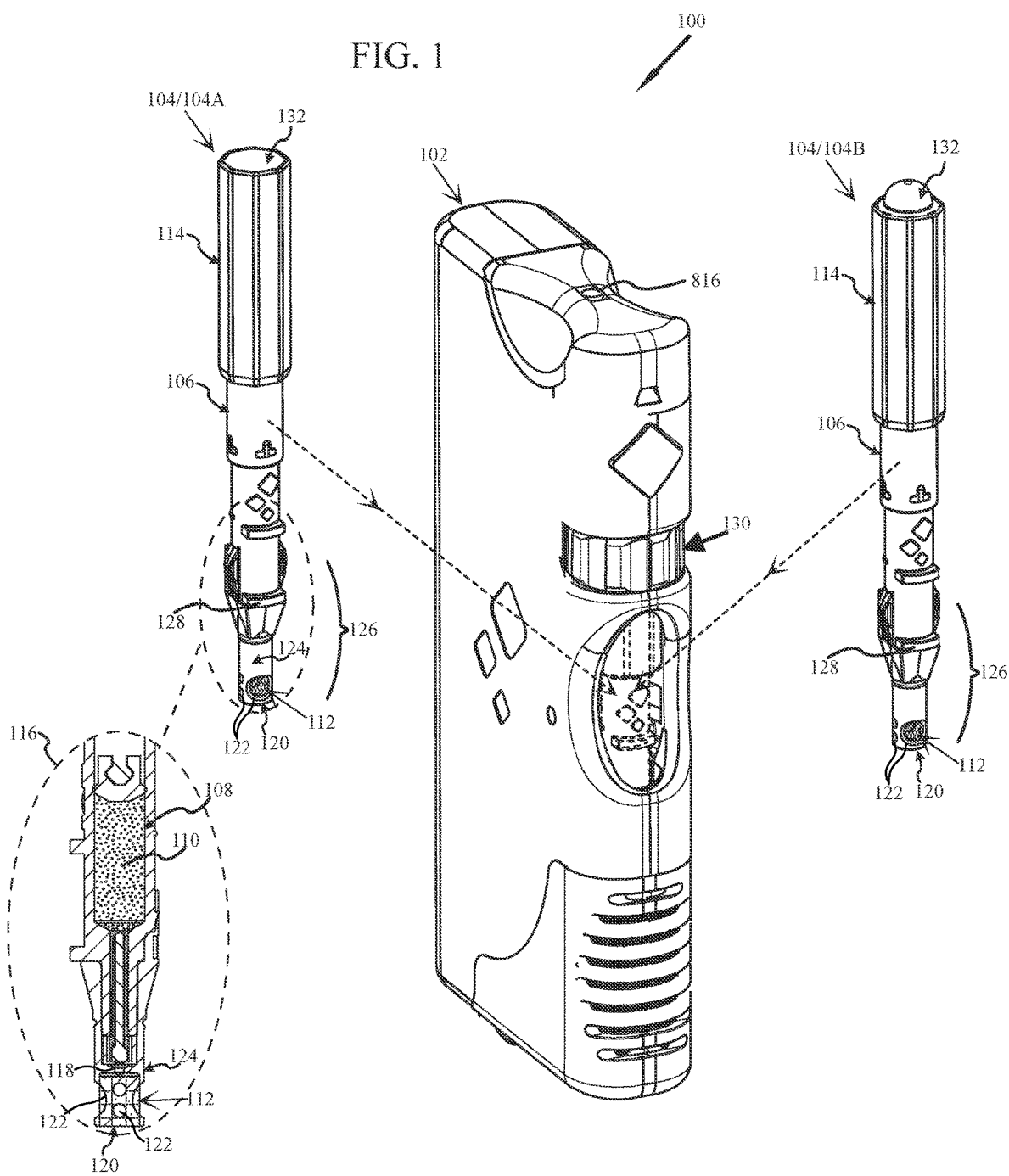
FIG. 1 illustrates a perspective view of a vaporizing device with a vaporizing cartridge system with diffuser in accordance with at least one embodiment of the present invention.

FIGS. 4A-4B present conceptual side cut through illustrations of a vaporizing cartridge with diffuser having a longitudinal plunger and an exploded view of same in accordance with at least one embodiment of the present invention;

FIGS. 5A-5B present conceptual side cut through illustrations of the vaporizing cartridge with diffuser of FIG. 4A initially at rest and then in a dispensing state in accordance with at least one embodiment of the present invention;

FIGS. 6A-6B present conceptual side cut through illustrations of the vaporizing cartridge with diffuser of FIG. 4A re-priming the pump cavity and then again at rest awaiting the next dispensing activation in accordance with at least one embodiment of the present invention;

FIG. 7 is a high level flow diagram of a method for using a vaporizing cartridge with diffuser in accordance with at least one embodiment of the present invention; and FIGS. 8A-8D are conceptual block diagrams illustrating the method of use as presented in FIG. 7.

DETAILED DESCRIPTION

Before proceeding with the detailed description, it is to be appreciated that the present teaching is by way of example only, not by limitation. The concepts herein are not limited to use or application with a specific system or method for providing or using a removable vaporizer system. Thus, although the instrumentalities described herein are for the convenience of explanation shown and described with respect to exemplary embodiments, it will be understood and appreciated that the principles herein may be applied equally in other types of systems and methods for removable vaporizer cartridges and vaporizing liquids and concentrates with vaporizer devices.

This invention is described with respect to preferred embodiments in the following description with reference to the Figures, in which like numbers represent the same or similar elements. Further, with respect to the numbering of the same or similar elements, it will be appreciated that the leading values identify the Figure in which the element is first identified and described, e.g., element 100 first appears in FIG. 1.

Tuning now to FIG. 1, there is shown a vaporizing cartridge system 100 essentially comprising a vaporizing device 102 and a removable "Vaporizing Cartridge with Diffuser" 104, hereinafter VCD 104. As shown, VCD 104 is intended to be inserted into the vaporizing device 102. The VCD 104 is a sealed device, which is to say that prior to insertion in a vaporizing device 102, or following removal from a vaporizing device 102, the VCD 104 is structured and arranged to safeguard the concentrate product that is inside the VCD 104.

As is further discussed below, varying embodiments for advantageous dosage control are presented as two optional embodiments—a screw plunger embodiment of VCD 104 is shown as VCD 104A, and a longitudinal plunger embodiment of VCD 104 is shown as VCD 104B.

In general, VCD 104 is comprised of a housing 106, a reservoir 108 of liquid concentrate 110 within the housing (shown as dots), a diffuser element 112 and a metered dispenser 114 that is structured and arranged to dispense from the reservoir 108 into the diffuser element 112 a predetermined amount of liquid concentrate 110. The reservoir 108, liquid concentrate 110, and diffuser element 112 may be further appreciated in the partial cut away view 116, in which is also shown a first one-way valve 118.

The term "concentrate," as used herein, may include substances in the form of chemicals, distillates, and isolates. Examples of the concentrate include vaporizable medications, such as tetrahydrocannabinol (THC), terpenes, cannabidiol (CBD), and other constituents of cannabinoids. Other examples of the concentrate include dry herbs, essential oils, waxes, and loose leaves. Moreover, different embodiments of VCD 104 may provide very different liquid concentrates 110, the liquids ranging in viscosity from that of low viscosity such as water or alcohol to high viscosity such as waxes and thick oils. In many instances, the liquid concentrate 110 may be of a type wherein exposure to air is undesirable for a variety of reasons, including but not limited to drying and oxidation. As such, it is an aspect of at least one embodiment of the present invention to provide an air tight seal for reservoir 108 so as to preserve the liquid concentrate 110 therein.

Moreover, in sharp contrast to traditional vaporizing devices 102 that include a diffuser element internally that must be periodically cleaned or replaced, and upon which all utilized liquid concentrates are disposed—and thereby at least partially cross contaminated, VCD 104 advantageously incorporates the diffuser element 112 as part of the removable cartridge. As such, as each VCD 104 is replaced, a new and fresh diffuser element 112 is provided to the vaporizing device 102—thus substantially reducing the opportunity for cross mixing or contamination of different vaporizing concentrates, as well as reducing the buildup of concentrate residue.

Returning to the VCD 104, the diffuser element 112 is structured and arranged to receive the liquid concentrate 110 and present it proximately to a heat source provided by the vaporizing device 102 such that the liquid concentrate 110 it may be vaporized. Surface tension of the liquid concentrate 110 and choice of materials, such as but not limited, to metal, glass, ceramic or composite screens, perforated sheets, or woven constructs permit the diffuser element 112 to receive, and in at least one embodiment, wick the liquid concentrate across/throughout the diffuser element 112 to promote uniform and substantially consistent vaporization.

For at least one embodiment, the diffuser element 112 is metal, such as but not limited to, gold, stainless steel, brass or tungsten steal. For yet another embodiment the diffuser element 112 is glass or glass fiber. For still yet another embodiment, the diffuser element 112 is synthetic or organic fiber. It will also be understood and appreciated that as different embodiments of VCD 104 may provide different liquid concentrates, different diffuser elements 112 may be selected that are most suitable for the different liquid concentrates.

As such, VCD 104 advantageously permits the most suitable diffuser element to be paired with the liquid concentrate of a given VCD 104. In other words, for at least one embodiment the operation and efficiency of the vaporizing device 102 is improved as the need to provide a generic diffuser element suitable for many liquid concentrates, but not specifically optimized for one liquid concentrate is eliminated as each VCD 104 provides its own optimized diffuser element 112.

For at least one embodiment, the diffuser element 112 is disposed within a protective sleeve 124 as a porous insert at the distal end 120 of VCD 104, the protective sleeve 124 having one or more apertures 122 so as to permit the flow of air through and/or around the diffuser element 112. For at least one alternative embodiment, the diffuser element 112 may be provided as an exposed distal end 120 of the VCD 104. In varying embodiments, the distal end 120 section of VCD 104 may be understood and appreciated as a nozzle 126. For at least one embodiment, the VCD 104 provides an identifier 128 such as a computer chip (e.g. smart chip) or another element that may be read by a cartridge reader within the vaporizing device 102.

For embodiments of VCD 104 providing such an identifier 128, the identifier 128 may be used by the vaporizing device to identify the liquid concentrate 110 provided by the VCD 104, and more specifically, to control the heating element of the vaporizing device. Moreover, for at least one embodiment the identifier 128 advantageously permits optimized control of the vaporizing heating element for the specific liquid concentrate 110 provided by a given VCD 104 disposed within the vaporizing device 102.

As used herein and for ease of discussion and illustration, it is to be understood and appreciated that whether the liquid concentrate is disposed onto or into the diffuser element 112 is a matter of design choice regarding the nature of the material and structure of the diffuser element 112. As such, unless specifically stated otherwise, the terms "onto" or "into" may be used interchangeably with respect to how the liquid concentrate is provided to the diffuser element 112.

VCD 104 also advantageously ensures that the proper amount of liquid concentrate 110 is dispensed into the diffuser element 112, by advantageously employing a metered dispenser 114. As is set forth in greater detail below, for at least one embodiment this is achieved at least in part by a VCD 104 employing a mechanical threshold trigger. Simply stated, VCD 104 is structured and arranged to ensure that a user must apply at least a pre-determined threshold force before VCD 104 will be activated to dispense the predetermined amount of liquid concentrate. Indeed, it is an advantageous aspect of the present invention that if a user applies less than the threshold force, essentially no amount of liquid concentrate 110 is dispensed. As such, for each activation of VCD 104 there is a high degree of certainty that the predetermined amount of liquid concentrate 110 is being dispensed.

It is also to be understood and appreciated that different embodiments of VCD 104 may be provided to permit different amounts of different liquid concentrates to be dispensed. In other words, a first VCD 104 having a first liquid concentrate may be structured and arranged to dispense a first predetermined amount of liquid concentrate, and a second VCD 104 having a second liquid concentrate may be structured and arranged to dispense a second predetermined amount of liquid concentrate that is different from the first predetermined amount of liquid concentrate.

Moreover, VCD 104 and indeed vaporizing system 100 advantageously permits users to receive different predetermined dosages of liquid concentrate for various different products. And as the dosing amount is determined by the VCD 104, such advantageous adaptability to provide different dosing amounts is achieved without requiring user adjustment or reconfiguration of the vaporizing device 102.

The vaporizing device 102 has an internal heating element (not shown), which is proximate to a VCD 104 receiving port (internal and not shown) and a dispensing trigger 130 that is structured and arranged to engage with VCD 104 to dispense a predetermined amount of the liquid concentrate 110 into the diffuser element 112. For at least one embodiment the dispensing trigger 130 is a wheel which is rotated by a user to initiate the dispensing of the liquid concentrate. For at least one other embodiment, the dispensing trigger is a press level.

Although for at least some embodiments, vaporizing devices 102 may be preconfigured for operation specifically with either a wheel or a press level as a dispensing trigger 130, thus requiring a corresponding VCD 104 operable with either a wheel or a level dispensing trigger 130, for at least one alternative embodiment, a vaporizing device 102 may provide both a wheel and a press level as dispensing triggers 130, or a combined wheel and press lever—the operable behavior configured by the mechanical interface of the VCD 104 when disposed within the vaporizing device 102.

To briefly summarize, for at least one embodiment, provided is a vaporizer cartridge system 100 including: a vaporizing device 102 providing a heating element 802 proximate to a removable cartridge system receiving port 804, and a dispensing trigger 130 structured and arranged to engage a removable vaporizing cartridge with diffuser 104 disposed in the receiving port 804 to dispense a predetermined amount of a liquid concentrate 110 from within the removable vaporizing cartridge with diffuser 104; at least one removable vaporizing cartridge with diffuser 104 including: a housing 106; a reservoir 108 of liquid concentrate 110; a diffuser element 112; a metered dispenser 114 structured and arranged to dispense from the reservoir 108 into the diffuser element 112 a predetermined amount of liquid concentrate 110.

For at least one embodiment, the metered dispenser 114 is implemented with several elements cooperatively interacting, including a first one-way valve 118 disposed between the reservoir 108 and the diffuser element 112 and a dispensing plunger 132 structured and arranged to apply a pre-determined force upon the reservoir to dispense from the first one-way valve 118 a predetermined amount of liquid concentrate into the diffuser element 112. At least two configurations for the dispensing plunger 132 may be adapted for varying embodiments of VCD 104. Each will be summarized and then presented in greater detail below.

First, in at least one embodiment, the dispensing plunger 132 is a screw plunger, the dispensing trigger 130 structured and arranged to operably induce a degree of rotation to the screw plunger, the degree of rotation preselected to advance the screw plunger against the liquid concentrate of the reservoir to dispense the predetermined amount of liquid concentrate. In other words, the screw plunger rotates about a longitudinal axis with threads about the screw plunger engaging with threads within a housing such that the screw plunger advances towards the reservoir of liquid concentrate with each partial rotation. Such a dispensing plunger and reservoir configuration is set forth and described in PCT/US19/28541 entitled "Improved Vaporizer, System, and Method for Managing Concentrate Usage"—corresponding to U.S. Patent Application 17,047,204 published as US 2021/0161213 incorporated herein by reference.

Second, in at least one alternative embodiment, the dispensing plunger 132 is a longitudinal plunger, moving up and down along a longitudinal axis to activate an airless pump. To briefly summarize, for at least one embodiment an airless pump is provided by a pump cavity defined by a pump top and a pump bottom, the first one-way valve 118 disposed at the pump bottom, a second one-way valve disposed at the pump top and in fluid communication with the reservoir, a coil spring disposed about the pump cavity. The longitudinal movement of the longitudinal plunger operates the pump cavity in two phases.

First, the pump cavity is compressed such that liquid concentrate within the pump cavity is disposed from the first one-way valve 118 at the bottom into the diffuser element. Second, as the longitudinal plunger returns to its non-depressed state, the pump cavity expands and draws in liquid concentrate through the second one-way valve at the top from the reservoir of liquid concentrate. An upper floating seal of the reservoir maintains the sealed integrity of the reservoir and moves towards the pump cavity until the reservoir is depleted.

With respect to FIG. 1, a screw plunger embodiment of VCD 104 is shown as VCD 104A, and a longitudinal plunger embodiment of VCD 104 is shown as VCD 104B. As illustrated in FIG. 1, it will be understood and appreciated that embodiment variations of the dispensing plunger do not affect the diffuser element 112.

FIG. 2A provides a side cut through view of an embodiment for VCD 104A, the rotating screw plunger 200. As shown, a rotating driver 202 such as a threaded sleeve or nut is disposed upon the rotating screw plunger 200 which rotates about longitudinal axis 204. External threads 206 are provided around at least a portion of the plunger shaft—essentially and substantially as threads about a bolt. External threads 206 engage with internal threads 208 disposed within the top portion of the housing 106. For the embodiment as shown, the plunger tip 210 is coupled to a plunger seal 212 that defines a movable end of the reservoir 108. With such a configuration of elements, it will be appreciated that as the rotating screw plunger 200 is rotated, it will advance and drive the plunger seal 212 towards the diffuser element 112 and thereby cause liquid concentrate to be dispensed.

With such a configuration, the dispensing trigger 130 (see FIG. 1) of the vaporizing device is structured and arranged to impart a degree of rotation to the screw plunger is a rotating wheel. For at least one embodiment, such rotation is achieved by providing a dispensing trigger 130 in the form of a rotating wheel, commonly referred to with such devices as a dosing wheel. For yet another embodiment, such rotation may be employed with a dispensing trigger substantially similar to the mechanism of a ball point pen, wherein an angled tooth cam translates longitudinal motion of the trigger into incremental rotation. As it may not be desirable to laterally translate the VCD 104 within the vaporizing device 102, additional springs and cams may be employed to remove lateral motion of the VCD 104.

For yet another embodiment as noted, the dispensing trigger 130 is a rotating wheel. Such a rotating wheel may be biased by one or more springs of levers engaging longitudinal grooves in the rotating wheel, such that a predetermined threshold force must be applied to impart a rotation to the wheel. Such a threshold may be predetermined to ensure that each partial rotation of the rotating wheel is an intentional and complete act. In varying embodiments, the rotating wheel may be configured for different increments of partial rotation, such as between 4 and 18 increments of partial rotation. For at least one embodiment, the rotating wheel is configured for 6 partial rotations. For at least one alternative embodiment, the rotating wheel is configured for 12 partial rotations.

With each partial rotation of the rotating wheel, the rotating driver 202 imparts a partial rotation 214 to the rotating screw plunger 200, which by virtue of the engaged external threads 206 and internal threads 208 advances the plunger seal 212 within the reservoir 108, along longitudinal axis 204 (as shown by arrows 216) towards the diffuser element 112. Such incremental advancement drives liquid concentrate 110 out of the first one-way valve 218 and into the diffuser element 112. The one-way valve 218 may be an elastomer (silicone rubber, TPE, etc.) or other flexible, resilient material that has been structured and arranged to permit liquid flow in only one direction.

The predetermined configuration for increments of partial rotation is directly related to the incremental advancement of the rotating screw plunger 200 and correspondingly the extrusion of liquid concentrate from the reservoir into the diffuser element 112, VCD 104 accurately and consistently dispenses pre-determined amounts of the liquid concentrate 110 with each partial rotation of the dispensing trigger 130.

For a first embodiment, as the rotating screw plunger 200 is rotated, and essentially screwed towards the diffuser element 112, the overall length of VCD 104 will be reduced. For at least one second embodiment, the rotating driver 202 is more fully appreciated as a sleeve which rotates about the lower portion of VCD 104, but otherwise remains in place. As the rotation is imparted from the rotating driver 202 to the rotating screw plunger 200, the rotating screw plunger 200 moves within the rotating driver 202 sleeve towards the diffuser element 112 while the overall length of VCD 104 remains essentially constant.

For at least one embodiment, the dispensing end of VCD 104 is configured as a nozzle 220, with a channel 222 between the reservoir 108 and the first one-way valve 218, such that primary volume of the reservoir 108 is effectively set back up in the housing 106 and away from the diffuser element 112. Such a configuration may be desired so as to more effectively thermally isolate the reservoir 108, and more importantly the liquid concentrate 110, from the heat as applied to the diffuser element 112.

In addition, for at least one embodiment, a nozzle insert 224 may be disposed within the channel 222, as shown in enlarged cross section 226. In varying embodiments this nozzle insert 224 may be provided for the additional benefits of, but not exclusively limited to, reducing the volume of stagnant liquid concentrate 110 within the channel 222 between periods of VCD 104, for further thermal isolation, to assist with activation of the one-way valve 218, and combinations thereof.

Also shown in enlarged cross section 226 is an identifier 128. For at least one embodiment, the identifier 128 is at least partially embedded in the housing 106, such that external electrical contacts are provided to permit a vaporizing device 102 to read the smart chip provided as the identifier 128. For yet another embodiment, the identifier may be an image that is read by the vaporizing device 102. For still yet another embodiment, the identifier may be one or more physical structures that depress one or more pins provided by the vaporizing device to mechanically provide a code to identify the VCD 104.

As advancement of the rotating screw plunger 200 is intended to be permitted only in one direction—for the advancement of the plunger seal 212, VCD 104A includes a one way ratchet or pawl 228. As shown in FIG. 2B, for at least one embodiment, a one way ratchet or pawl 228 is provided by inner flanges 230 of the housing 106 being disposed inward against the rotating screw plunger 200 so as to engage with longitudinal slots or grooves 232 disposed in the rotating screw plunger 200.

FIGS. 3A and 3B provides an enlarged partial cross section of VCD 104A. FIG. 3 conceptually illustrates VCD 104A at rest with the plunger seal at a first elevation 300, thus defining a first volume for the reservoir 108. The first one-way valve 218 is closed and the liquid concentrate 110 is held within the reservoir 108 and channel 222.

In FIG. 3B, the user has initiated an action to dispense a metered amount of liquid concentrate 110, as is shown by the rotation arrows 302, which as discussed above are translated to longitudinal motion 304 of the plunger seal 212 towards the diffuser element 112. Moreover, it is appreciated from FIG. 3B, that the plunger seal 212 has advanced to a second elevation 306. The corresponding change 308 between the first elevation 300 and the second elevation 306 is a pre-determined change accomplished at least in part by the pitch of the internal and external threads 208 & 206, and the degree of measured rotation imparted by the threshold dispensing trigger 130.

Accordingly, the volume of the reservoir 108 has decreased by the lateral cross sectional area of the reservoir and the change 308 of elevation. More specifically, as the volume of the reservoir has decreased, pressure within the reservoir 108 has increased, and by pre-determined design is sufficient to activate the one-way valve 218 so as to be expelled from the reservoir 108 and channel 222 into the diffuser element 112, as shown by dots representing the liquid concentrate 110 now appearing in the diffuser element 112. With the pressure released, the first one-way valve 218 will close, thus providing the metered dose of liquid concentrate to the diffuser element 112.

With respect to FIGS. 3A and more specifically 3B, it is understood and appreciated that although the VCD 104/104A may be disposed within a vaporizing device 102 at the time a metered amount liquid concentrate 110 is dispensed into the diffuser element 112, as the diffuser element 112 is an integrated component of VCD 104/104A, the diffuser element 112 is not a component of the vaporizing device 102. More specifically, the metered amount liquid concentrate 110 has not left the VCD 104/104A to be disposed within the vaporizing device 102. However, the metered amount liquid concentrate 110 may now be vaporized by the vaporizing device 102.

FIGS. 4A through 6B illustrate yet another embodiment, wherein the metered dispenser 114 is an airless pump. Airless pumps typically operate by inducing a vacuum to dispense liquids, and are therefore well sealed and air tight. Whereas for the rotating screw plunger embodiment of VCD 102A shown above, a plunger seal 212 was attached to, or otherwise a component of the end of the screw plunger 200, for an airless pump a floating seal defines the upper end of the reservoir 108.

FIG. 4A presents an assembled conceptual embodiment of VDC 104B, and FIG. 4B presents a corresponding exploded view, though the scale has been adjusted for ease of illustration. For at least one embodiment the metered dispenser 114 is provided with a dispensing plunger 400 upon which an activation force is applied. For the dispensing plunger 400 having a movable shaft 402 with a top portion presenting as a push button 404.

The movable shaft 402 may have a circumferential groove so as to be actively coupled with a Belville spring 406 that is engaged with a portion of the housing 106 when the dispensing plunger 400 is received into the housing 106. For the conceptual embodiment as shown, the reservoir 108 is provided by the inner wall 408 of the dispensing plunger 400, a floating seal 412, and the top portion 410 of a pump cavity 414 provided by a pump top 416 and a pump bottom 418, a first one-way 420 valve disposed at the pump bottom 418 and a second one-way valve 422 disposed at the pump top in fluid communication with the reservoir 108.

The distal end 424 of the dispensing plunger 406 is coupled to a bottom seat 426 that is structured and arranged to slideably engage with lower annular wall 428 upon which is seated a coil spring 430. Nested over the coil spring 430, and descending along the inner portion of the coil spring 430 and slideably engaging with the inner surface of lower annular wall 428 is the sleeve 432 of the pump cavity 414. Sleeve 432 provides the pump top 416 in which the second one-way valve 422 is disposed. At rest, the pump cavity 414 has a first volume determined at least in part by its lateral cross sectional area and initial height 432.

FIG. 5A shows VCD 104B in an initialized state and at rest. The pump cavity 414 has been primed such that there is now some liquid concentrate 500, shown as slightly larger dots than the dots conceptualizing liquid concentrate 110. The initial height of the pump cavity is shown as height dimension 434. As illustrated by small force arrows 502, unless a threshold force is applied to the push button 404, the dispensing plunger 400 remains at rest, as the preselected threshold of the Belville spring 406 has not been overcome.

In FIG. 5B a force equal to or greater than the threshold force has been applied as exemplified by large force arrows 504. As such, the Belville spring 406 has deformed allowing the dispensing plunger 400 to move longitudinally towards the diffuser element 112, moving the bottom seat 426 along the lower annular wall 428 and inducing pressure upon the pump cavity 414 such that the first one-way valve 118/420 opens to release liquid concentrate 500 from the pump cavity 414 into the diffuser element 112, the released liquid concentrate 506 now in the diffuser element 112 shown as larger dots 506. The coil spring 430 is also compressed.

In the compressed state, the second height 508 of the pump cavity has been reduced from the initial height 432. It will be understood and appreciated that the volume of liquid concentrate 110 dispensed is related to this change 510 between the initial height 432 and second height 508. As such, various embodiments of VCD 104B may be designed with different cross sectional areas and/or different second heights so as to provide different pre-determined amounts of liquid concentrate 110 to be dispensed.

In FIG. 6A, the threshold force shown in FIG. 5B has been released, and as such, coil spring 430 expands to drive the pump cavity 414 back to its initial state. This action induces a vacuum within the pump cavity 414, effectively closing the first one-way valve 420 and causing the second one-way valve 422 to open and draw liquid concentrate 110 from the reservoir into the pump cavity 414. This vacuum also draws floating seal 412 downward as liquid concentrate 500 refills the pump cavity from the reservoir 108.

As shown in FIG. 6B, when expanded back to the initial state, both the first one way valve 420 and the second one-way valve 422 are closed, and the floating seal 412 has moved to a new position within the housing 106, the change 600 in location representing the volume of liquid concentrate 110 drawn from the reservoir 108 into the pump cavity 414. The first one-way valve 420 and the second one-way valve 422 as well as the floating seal 412 may be an elastomer (silicone rubber, TPE, etc.) or other flexible, resilient material that has been structured and arranged to permit liquid flow in only one direction.

As noted above, an VCD 104/104B is structured and arranged to provide accurate and consistent metered dispensation of the liquid concentrate 110. This is achieved at least in part by a threshold trigger requiring a predetermined force to be applied to achieve movement of the dispensing plunger 400.

For at least one embodiment, this threshold trigger is achieved with the Belleville spring 406 disposed about the movable shaft 402. Belleville spring 406 may also be described as a Belleville washer, coned-disc spring, conical spring washer, or disc spring cupped spring washer without departing from the scope and intention of the present invention. More specifically, the Belleville spring 406 is preselected to resist loading along its axis, until at least a predetermined force is applied. When such a force is applied, the Belleville spring 406 deforms and permits the longitudinal motion of the movable shaft 402. When the force is removed, the Belleville spring 406 regains its initial form, and thereby elevates the movable shaft 402 as well back to its initial state.

It will be appreciated that the movement of the movable shaft 402, and more specifically the dispensing plunger 400 is not great in comparison to the overall length of VCD 104/104B. As such, it will be appreciated that the minimum loading force to activate the Belleville spring 406 may be selected to ensure that longitudinal activation of the dispensing plunger 400 is an intentional and complete act.

As an alternative to the Belleville spring 406, for at least one alternative embodiment, the movable shaft 402 may have a circumferential groove and one or more spring loaded balls or pins may be disposed partially against, or into this groove from sleeves mounted in the housing 106. Angular arrangement between the contacting surfaces of the movable shaft 402, balls and pins, as well as spring force may be pre-selected to ensure that a preselected minimum force is applied to the push button 404 of movable shaft 402 to ensure that longitudinal activation of the dispensing plunger 400 is an intentional and complete act.

Although not shown in FIGS. 4A through 6B for ease of illustration and discussion, it should be understood and appreciated that for at least one embodiment, nozzle of VCD 104/104B may include an internal channel and nozzle insert as shown and described above with respect to FIG. 2.

As noted with respect to FIGS. 3A and 3B above, with respect to FIGS. 5B through 6B and more specifically 6B, it is understood and appreciated that although the VCD 104/104B may be disposed within a vaporizing device 102 at the time a metered amount liquid concentrate 110/506 is dispensed into the diffuser element 112, as the diffuser element 112 is an integrated component of VCD 104/104B, the diffuser element 112 is not a component of the vaporizing device 102. More specifically, the metered amount liquid concentrate 110/506 has not left the VCD 104/104B to be disposed within the vaporizing device 102. However, the metered amount liquid concentrate 110/506 may now be vaporized by the vaporizing device 102.

To summarize the above, for at least one embodiment, provided is a vaporizer removable cartridge system including: a housing 106; an airless pump with a reservoir 108 of liquid concentrate 110 at least partially disposed within the housing 106; a diffuser element 112; a mechanical threshold dispensing trigger 130 structured and arranged to require a predetermined threshold force to be applied before the trigger transfers directs force upon the airless pump to dispense a predetermined amount of liquid concentrate 110 into the diffuser element 112; wherein the removable cartridge is structured and arranged to be removably disposed within a vaporizing device 102 providing a heating element 802 proximate to the diffuser element 112, the vaporizing device 102 further providing a dispensing trigger 130 structured and arranged to engage the dispensing plunger 132/200/400 of the removable cartridge.

Having described embodiments for a vaporizing system 100, and more specifically VCD 104 as shown with respect to FIGS. 1-6B, other embodiments relating to varying methods of vaporizing liquid concentrate with a portable vaporizing device advantageously structured and arranged to accept a VCD 104 now be discussed with respect to FIGS. 7 and 8A-8D in connection with FIGS. 1-6B. Moreover, FIG. 7 is a flow diagram illustrating an embodiment of method 700 for vaporizing a liquid concentrate, and FIGS. 8A-8D are conceptual block diagrams, simplifying the elements, and demonstrating the vaporizing method in connection with at least one VCD 104. It will be appreciated that the described method need not be performed in the order in which it is herein described, but that this description is merely exemplary of one method of determining appropriate dosage for a product in accordance with the present invention.

As shown, method 700 traditionally begins with the user receiving a first VCD 104, block 702. The VCD 104 is then at least partially inserted into a vaporizing device 102/800, the vaporizing device having at least a heating element 802 proximate to a receiving port 804, and a dispensing trigger 806, block 704. In various embodiments, vaporizing device 102 may also have at least one cartridge reader 808, a controller 810 such as a such as Central Processing Unit (CPU) with at least one microprocessor and associated memory, and a power supply 812. Vaporizing device 102 also provides at least one air entry port 814, and a vapor dispensing port 816 interconnected by an air passage way.

As shown in FIGS. 8A-8D, for at least one embodiment, the vaporizing device 102 has a cartridge reader 808, and as such, method 700 optionally proceeds to read the identifier 128 from the VCD 104, optional block 706. Controller 810, locally, or with the aid of a remote system communicated with by wireless network protocols, interprets the identifier 128 to identify the optimum heating control for heating element 802, optional block 708.

The user initiates a metered dispensation of the liquid concentrate 110 from the reservoir 108 by activating the dispensing trigger 130/806, block 710. As a result, the reservoir 108 is influenced to expel a measured amount of the liquid concentrate 110 through the first one-way valve 118 and into the diffuser element 112, as shown in FIG. 8B.

Figure 8A:
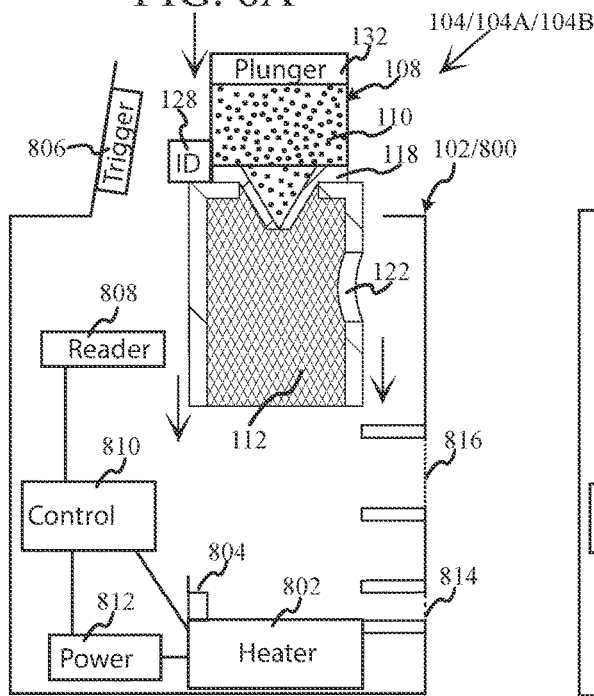
Figure 8B:
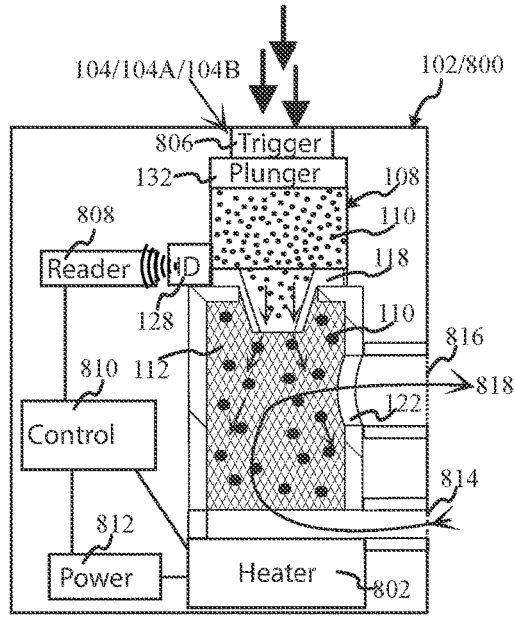

As is also shown in FIG. 8B, the diffuser element and protective sleeve 124 provide elements of the air passage 818 within the vaporizing device 102. Moreover, air is permitted into the vaporizing device 102 through air entry port 814 and directed to the heating area, through the diffuser element, and then out a vapor dispensing port 816. More specifically, when disposed within a vaporizing device 102, VCD 104, provides a portion of the air flow pathway.

Figure 8C:
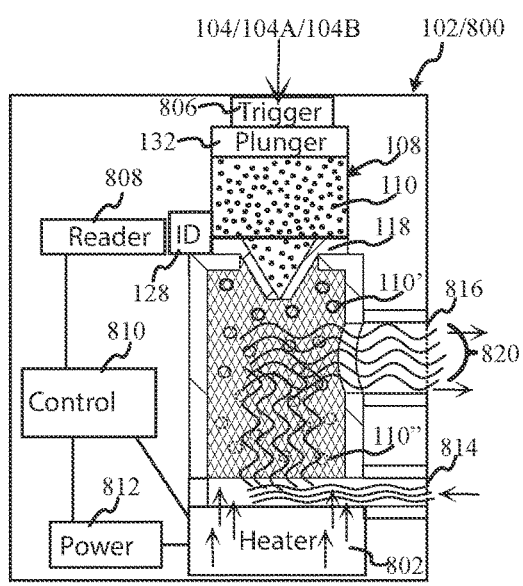

With the liquid concentrate 110 now dispensed into the diffuser of the VCD 104, as shown in FIG. 8C, the controller 810 activates the heating element 802, block 712. For at least one embodiment this heating control is achieved by controlling the amount and duration of electrical current provided by power source 812 to the heating element 802. In varying embodiments as noted above, the controller 810 may operate the heater for specific durations, heat intensity, and or gradual heating and cooling. For at least one embodiment, based on the identifier 128, the controller 810 operates the heating element 802 in the optimum fashion to achieve maximum vaporization of the liquid concentrate 110.

Moreover, as shown in FIG. 8C, the liquid concentrate 110 within the diffuser element is vaporizing—represented by lighter line circles 110', and dotted line circle 110". The flow of vapor 820 exiting from the vapor dispensing port 816 now contains vaporized liquid concentrate.

Method 700 permits the user to re-use the currently inserted VCD 104 if the user so desired, decision 714. Should the user so desire, method 700 returns to block 710 with the active activation of the dispensing trigger.

Method 700 also permits the user to opt to remove the VCD 104 and install a second VCD 104, decision 716. With the insertion of a new second VCD 104, method 700 returns to block 704, and the optional process of reading the identifier 128 from the second VCD 104, optional block 706.

Moreover, in addition to specifically controlling the heating element 802, for at least one embodiment, the heating element 802 is controlled to heat to a specific first temperature for a first liquid concentrate 110, and to heat to a specific second temperature for a second liquid concentrate 110.

Figure 8D:
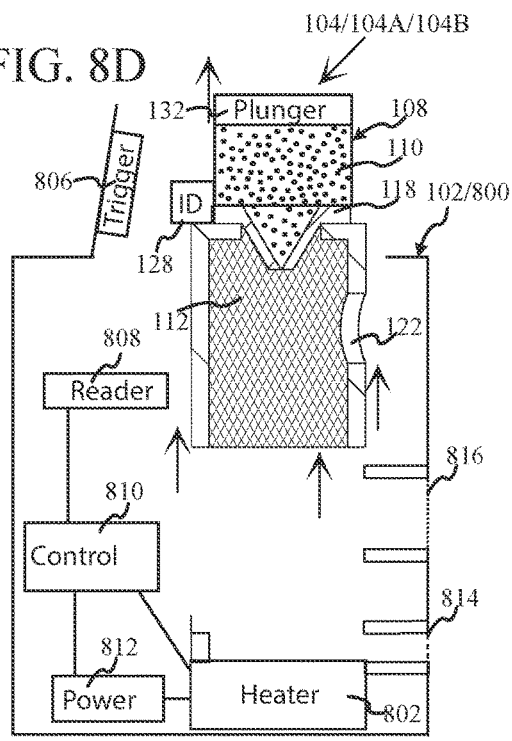

As show in FIG. 8D, and as noted above, although the VCD 104 may be disposed within a vaporizing device 102/800 at the time a metered amount liquid concentrate 110 is dispensed into the diffuser element 112, as the diffuser element 112 is an integrated component of VCD 104, the diffuser element 112 is not a component of the vaporizing device 102. More specifically, the metered amount liquid concentrate 110 has not left the VCD 104 to be disposed within the vaporizing device 102.

Various embodiments presented herein are descriptive of apparatus, systems, articles of manufacturer, or the like for systems and methods involving providing a certificate by way of a browser extension. In some embodiments, an interface, application browser, window or the like may be provided that allows the user of the computing device to direct behavior of the computing device.

Moreover, some portions of the detailed description above are presented in terms of the manipulation and processing of data bits within a computer memory. The steps involved with such manipulation are those requiring the manipulation of physical quantities. Generally, though not necessarily, these quantities take the form of electrical or magnetic signals capable of being stored, transferred, combined, compared and otherwise manipulated. Those skilled in the art will appreciate that these signals are commonly referred to as bits, values, element numbers or other clearly identifiable components.

It is of course understood and appreciated that all of these terms are associated with appropriate physical quantities and are merely convenient labels applied to these physical quantifies. Moreover, it is appreciated that throughout the following description, the use of terms such as "processing" or "evaluating" or "receiving" or "outputting" or the like, refer to the action and processor of a computer system or similar electronic computing device that manipulates and transforms data represented as physical (electrical) quantities within the computer system's memories into other data similarly represented as physical quantities within the computer system's memories.

The present invention also relates to apparatus for performing the operations herein described. This apparatus may be specifically constructed for the required purposes as are further described below, or the apparatus may be a general purpose computer selectively adapted or reconfigured by one or more computer programs stored in the computer upon computer readable storage medium suitable for storing electronic instructions.

Changes may be made in the above methods, systems and structures without departing from the scope hereof. It should thus be noted that the matter contained in the above description and/or shown in the accompanying drawings should be interpreted as illustrative and not in a limiting sense. Indeed, many other embodiments are feasible and possible, as will be evident to one of ordinary skill in the art. The claims that follow are not limited by or to the embodiments discussed herein, but are limited solely by their terms and the Doctrine of Equivalents.

What is claimed:

1. A vaporizer cartridge system comprising:
    a vaporizing device providing a heating element proximate to a receiving port for receiving a removable vaporizing cartridge with diffuser, and a dispensing trigger structured and arranged to engage the removable vaporizing cartridge with diffuser disposed in the receiving port to dispense a predetermined amount of a liquid concentrate from within the removable vaporizing cartridge with diffuser;
    at least one removable vaporizing cartridge with diffuser including:
        a housing;
        a reservoir of liquid concentrate;
        a diffuser element;
        a metered dispenser structured and arranged to dispense from the reservoir into the diffuser element the predetermined amount of liquid concentrate.

2. The vaporizer cartridge system of claim 1, wherein the metered dispenser comprises:
    a first one-way valve disposed between the reservoir and the diffuser element;
    a dispensing plunger structured and arranged to apply a pre-determined force upon the reservoir to dispense from the first one-way valve the predetermined amount of liquid concentrate into the diffuser element.

3. The vaporizer cartridge system of claim 2, wherein the dispensing plunger is a mechanical threshold trigger, a predetermined threshold force being required to achieve movement of the dispensing plunger.

4. The vaporizer cartridge system of claim 2, wherein the dispensing plunger is a screw plunger, the dispensing trigger of the vaporizing device operably inducing a degree of rotation to the screw plunger, the degree of rotation preselected to advance the screw plunger against the liquid concentrate of the reservoir to dispense the predetermined amount of liquid concentrate.

5. The vaporizer cartridge system of claim 2, further including a pump having a pump cavity defined by a pump top and a pump bottom, the first one-way valve disposed at the pump bottom, a second one-way valve disposed at the pump top and in fluid communication with the reservoir, a coil spring disposed about the pump cavity.

6. The vaporizer cartridge system of claim 5, wherein the dispensing plunger drives liquid concentrate from the reservoir into the pump cavity, compression of the pump cavity dispensing the predetermined amount of liquid concentrate into the diffuser element.

7. The vaporizer cartridge system of claim 2, wherein the dispensing trigger is a mechanical lever structured and arranged to engage the dispensing plunger.

8. The vaporizer cartridge system of claim 7, wherein the mechanical lever imparts a rotational force to the dispensing plunger.

9. The vaporizer cartridge system of claim 7, wherein the mechanical lever imparts a longitudinal force along a longitudinal axis of the dispensing plunger.

10. The vaporizer cartridge system of claim 1, wherein the vaporizing device provides an air passage conduit from the heating element to the diffuser element and from the diffuser element to a vapor dispensing port.

11. The vaporizer cartridge system of claim 1, wherein the vaporizing device has a cartridge reader structured and arranged to read information from the removable vaporizing cartridge with diffuser to control at least the heating element of the vaporizing device.

12. The vaporizer cartridge system of claim 1, wherein a first amount of concentrate disposed to a first diffuser element of a first removable vaporizing cartridge with diffuser is different from a second amount of concentrate disposed to a second diffuser element of a second removable vaporizing cartridge with diffuser.

13. A removable vaporizer cartridge comprising:
a housing;
a reservoir of liquid concentrate within the housing;
a diffuser element;
a first one-way valve disposed between the reservoir and the diffuser element;
a dispensing plunger structured and arranged to apply a pre-determined force upon the reservoir to dispense from the first one-way valve a predetermined amount of liquid concentrate into the diffuser element;
wherein the removable vaporizer cartridge is structured and arranged to be removably disposed within a vaporizing device providing a heating element proximate to the diffuser element, the vaporizing device further providing a dispensing trigger structured and arranged to engage the dispensing plunger of the removable vaporizer cartridge.

14. The removable vaporizer cartridge of claim 13, wherein the dispensing plunger is a mechanical threshold trigger, a predetermined threshold force being required to achieve movement of the dispensing plunger.

15. The removable vaporizer cartridge of claim 13, wherein the dispensing plunger is a screw plunger, the dispensing trigger of the vaporizing device operably inducing a degree of rotation to the screw plunger, the degree of rotation pre-selected to advance the screw plunger against the liquid concentrate of the reservoir to dispense the predetermined amount of liquid concentrate.

16. The removable vaporizer cartridge of claim 13, further including a pump having a pump cavity defined by a pump top and a pump bottom, the first one-way valve disposed at the pump bottom, a second one-way valve disposed at the pump top and in fluid communication with the reservoir, a coil spring disposed about the pump cavity.

17. The removable vaporizer cartridge of claim 16, wherein the dispensing plunger drives liquid concentrate from the reservoir into the pump cavity, compression of the pump cavity dispensing the predetermined amount of liquid concentrate into the diffuser element.

18. The removable vaporizer cartridge of claim 13, further comprising an identifier structured and arranged to be read by a vaporizing device to determine information to control at least the heating element of the vaporizing device.

19. A method of vaporizing liquid concentrate with a portable vaporizing device, comprising:
receiving a first removable vaporizing cartridge having;
a housing;
a reservoir of liquid concentrate within the housing;
a diffuser element;
a first one-way valve disposed between the reservoir and the diffuser element;
a dispensing plunger structured and arranged to apply a pre-determined force upon the reservoir to dispense from the first one-way valve a predetermined amount of liquid concentrate into the diffuser element;
inserting at least a portion of the first removable vaporizing cartridge into a vaporizing device providing a heating element proximate to a receiving port structured and arranged to receive the first removable vaporizing cartridge, and a dispensing trigger structured and arranged to engage the dispensing plunger to dispense the predetermined amount of a liquid concentrate from within the removable vaporizing cartridge into the diffuser element;
activating the dispensing trigger to dispense the predetermined amount of liquid concentrate into the diffuser element; and
heating the diffuser element to vaporize the liquid concentrate into an air passage conduit from at least the diffuser element to a vapor dispensing port.

20. The method of vaporizing liquid concentrate of claim 19, wherein the dispensing plunger is a screw plunger, the dispensing trigger of the vaporizing device operably inducing a degree of rotation to the screw plunger, the degree of rotation pre-selected to advance the screw plunger against the liquid concentrate of the reservoir to dispense the predetermined amount of liquid concentrate.

21. The method of vaporizing liquid concentrate of claim 19, further including a pump having a pump cavity defined by a pump top and a pump bottom, the first one-way valve disposed at the pump bottom, a second one-way valve disposed at the pump top and in fluid communication with the reservoir, a coil spring disposed about the pump cavity.

22. The method of vaporizing liquid concentrate of claim 21, wherein the dispensing plunger drives liquid concentrate from the reservoir into the pump cavity, compression of the pump cavity dispensing the predetermined amount of liquid concentrate into the diffuser element.

23. The method of vaporizing liquid concentrate of claim 19, further comprising an identifier structured and arranged to be read by a vaporizing device to determine information to control at least the heating element of the vaporizing device.

24. The method of vaporizing liquid concentrate of claim 19, wherein a first amount of concentrate disposed to a first diffuser element of a first removable vaporizing cartridge is different from a second amount of concentrate disposed to a second diffuser element of a second removable vaporizing cartridge.

25. The method of vaporizing liquid concentrate of claim 19, wherein the dispensing plunger is a mechanical threshold trigger, a predetermined threshold force being required to achieve movement of the dispensing plunger.

\* \* \* \* \*